March 25, 1969 J. H. ASPER Plant Pat. 2,873
CAMELLIA PLANT
Filed Sept. 1, 1967
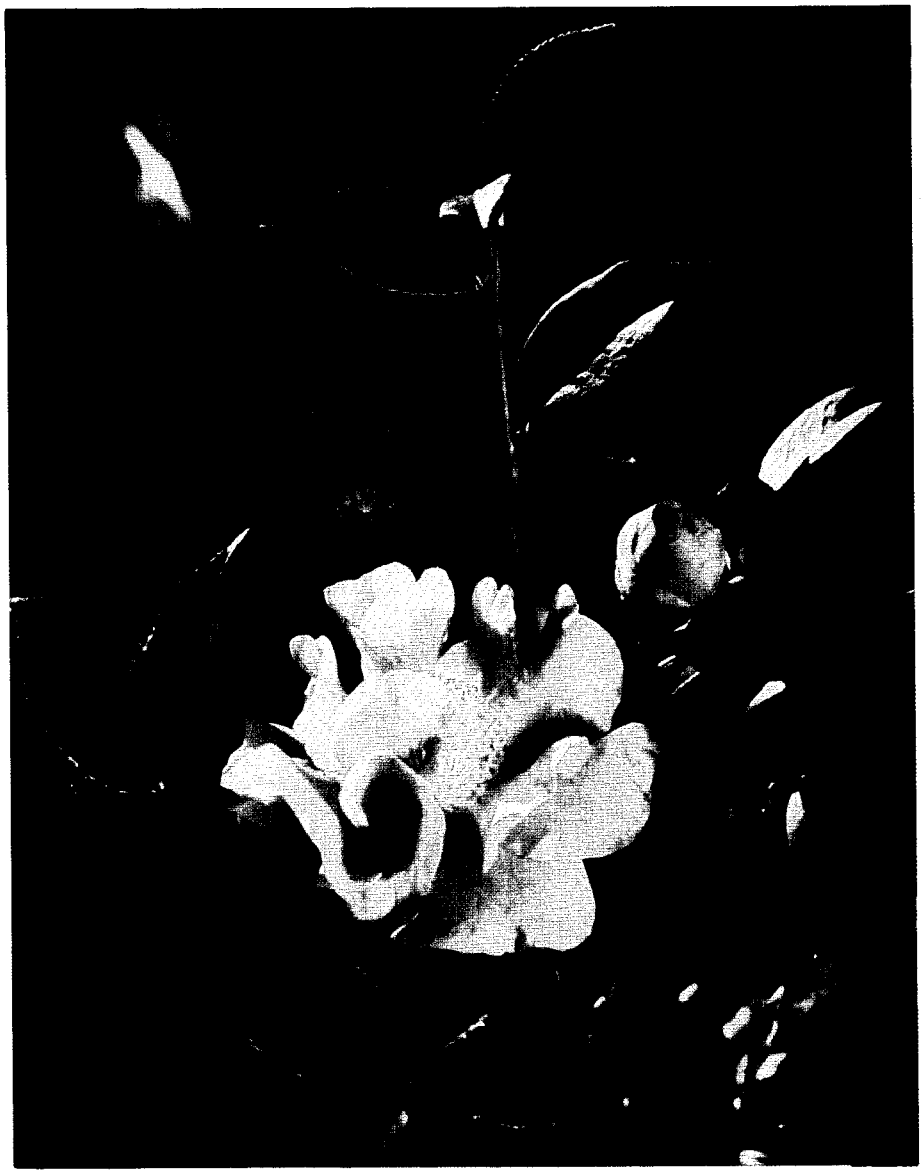
INVENTOR.
JAMES HOWARD ASPER
BY Rummler & Snow
ATTYS.

United States Patent Office

Plant Pat. 2,873
Patented Mar. 25, 1969

2,873

CAMELLIA PLANT

James Howard Asper, Escondido, Calif., assignor to Monrovia Nursery Company, Azusa, Calif., a corporation of California Filed Sept. 1, 1967, Ser. No. 665,188
Int. Cl. A01h 5/02
U.S. Cl. Plt.—61 1 Claim

ABSTRACT OF THE DISCLOSURE

A new camellia hybrid producing large flowers of a warm medium-pink color and having large, curled and loosely arranged petals; and characterized further by its vigorous growth habit and the early, profuse and continuous production of blooms in season.

BACKGROUND OF THE INVENTION

This new variety of camellia plant was discovered by me in 1960 in the course of a breeding program carried on by me at Escondido, Calif. since 1957 with the object of producing a more hardy camellia plant combining the plant vigor and blooming habit of *C. sasanqua* with the large flower and beauty of *C. reticulata*. The new plant originated as a seedling of *C. sasanqua* Narumigata (unpatented), as the seed parent, and *C. reticulata* Buddha (Plant Pat. 1,212) and was selected by me because of its close approach to my breeding objectives. This plant was asexually propagated by me at Escondido, Calif., by grafting and cuttings, and successive generations have shown its unusual and novel characteristics to be firmly fixed and to hold true from generation to generation.

DESCRIPTION OF THE DRAWING

This new variety of camellia plant is shown in the accompanying photographic drawing, in substantially natural color, in which a fully opened bloom appears, in face view, and a bud and foliage are also shown.

DESCRIPTION OF THE INVENTION

The following is a detailed description of my new hybrid camellia plant, the color designation for the bud and bloom being according to the Horticultural Colour Chart of the British Colour Council.

*The Plant*

Origin: Seedling.
Parentage:
- *Seed parent.*—*C. sasanqua* Narumigata (unpatented).
- *Pollen parent*—*C. reticulata* Buddha (Plant Pat. 1,215).

Classification: Hybrid.
Form: Bush.
Height: Eight feet.
Growth: Vigorous, sturdy and upright with strong branching,
Foliage:
- *Quantity.*—Abundant.
- *Size of leaf.*—3½ inches long, 1½ inches wide.
- *Shape of leaf.*—Lanceolate with serrated margins.
- *Texture.*—Leathery. Aspect—glossy.

- *Color.*—Upper side—dark green. Under side—light green.
- *Petioles.*—½ inch long.
- *Ribs and veins.*—Prominent.

*Bud*

Size: 1½ inches long, 1 inch in diameter.
Form: Ovoid. Opens slowly.
Color: Geranium Lake 20/2 when sepals first divide and when petals unfurl.
Sepals: Hooded over bud and branched. Color.—pale green, inside and outside.
Calyx: Broad and funnel-shaped with hairy aspect.
Peduncle: Erect and hairy, 1/16 inch long. Color.—pale green.

*The flower*

Blooming habit: Profuse and continuous, in fall and early winter in its natural habitat.
Size: Large, 5¾ inches in diameter and 3½ inches deep.
Borne: Singly.
Shape: Cup-shaped with high center,
Petalage:
- *Number of petals.*—16.
- *Arrangement.*—Loosely imbricated and curled.
- *Size.*—2¾ inches x 2 inches.
- *Color.*—Geranium Lake 20/2 throughout.
- *Appearance.*—Satiny.

Petaloids: None.
Peduncle: ¼ inch long. Sturdy and upright. Color—brownish-green.
Discoloration: Color lightens as flower ages.
Fragrance: Slight.
Lasting quality: Ten days on plant. Three days as cut flower.
Persistance: Flower does not hang on and dry. Flowers are not affected by hot or wet weather, and as observed at Escondido, Calif., they are not subject to disease.

*Reproductive organs*

Stamens:
- *Anthers.*—208 in number. Length—each 1/32 inch long. Arrangement—bunched.
- *Filaments.*—Length—¾ inch long. Color—yellow.

Pollen: Color—golden yellow.
Pistils: Three in number; one inch long.
Stigmas: Color—light green.
Ovaries: Pistils joined.

*Fruit*

The fruit of this new variety is fertile, round in shape and of brown color at maturity.

I claim:

1. A new and distinct variety of hybrid camellia plant substantially as herein shown and described, characterized by its large, warm medium pink blooms which appear early and profusely during the early fall to winter season, and by its vigorous habit of plant growth.

No references cited.

ROBERT E. BAGWILL, *Primary Examiner.*